(12) United States Patent
von Blumenthal et al.

(10) Patent No.: US 8,047,205 B2
(45) Date of Patent: Nov. 1, 2011

(54) GAS-MIXING DEVICE FOR RESPIRATORS

(75) Inventors: Tilman von Blumenthal, Lübeck (DE);
Judith Löser, Lübeck (DE); Ralf Lorenzen, Lübeck (DE); Bernhard Ludwig, Lübeck (DE); Frank Oelgarth, Divonne les Bains (FR)

(73) Assignee: Dräger Medical GmbH, Lübeck (DE)

( * ) Notice: Subject to any disclaimer, the term of this patent is extended or adjusted under 35 U.S.C. 154(b) by 1014 days.

(21) Appl. No.: 11/937,029

(22) Filed: Nov. 8, 2007

(65) Prior Publication Data

US 2008/0121233 A1    May 29, 2008

(30) Foreign Application Priority Data

Nov. 25, 2006 (DE) .................... 10 2006 055 779

(51) Int. Cl.
*A62B 7/00* (2006.01)

(52) U.S. Cl. .......... 128/205.11; 128/203.12; 128/203.25; 128/204.18; 128/205.24

(58) Field of Classification Search ............. 128/203.12, 128/203.25, 203.27, 204.18, 204.21, 204.22, 128/205.11, 205.13, 205.15, 205.16, 205.24, 128/207.12
See application file for complete search history.

(56) References Cited

U.S. PATENT DOCUMENTS

| | | | | |
|---|---|---|---|---|
| 3,762,428 A * | 10/1973 | Beck et al. | ...................... | 137/88 |
| 3,840,006 A * | 10/1974 | Buck et al. | ............... | 128/204.21 |
| 3,896,837 A * | 7/1975 | Rohling | ......................... | 137/110 |
| 4,022,234 A | 5/1977 | Dobritz | | |
| 4,072,148 A * | 2/1978 | Munson et al. | .......... | 128/205.11 |
| 4,121,578 A * | 10/1978 | Torzala | ..................... | 128/204.23 |
| 4,148,311 A * | 4/1979 | London et al. | ........... | 128/204.26 |
| 4,240,419 A * | 12/1980 | Furlong et al. | ............ | 128/204.23 |
| 4,313,436 A * | 2/1982 | Schwanbom et al. | ... | 128/203.12 |
| 4,345,610 A * | 8/1982 | Herter et al. | ....................... | 137/7 |
| 4,392,514 A * | 7/1983 | Farley et al. | ............... | 137/624.2 |
| 4,526,188 A * | 7/1985 | Olsson et al. | ....................... | 137/3 |
| 4,576,159 A * | 3/1986 | Hahn et al. | ............... | 128/203.14 |
| 4,651,728 A * | 3/1987 | Gupta et al. | ............. | 128/201.28 |
| 4,905,685 A * | 3/1990 | Olsson et al. | ............ | 128/203.12 |
| 4,919,124 A * | 4/1990 | Stevenson et al. | ....... | 128/202.26 |
| 5,159,924 A * | 11/1992 | Cegielski et al. | ........ | 128/203.12 |
| 5,237,987 A * | 8/1993 | Anderson et al. | ........ | 128/204.18 |
| 5,383,449 A * | 1/1995 | Forare et al. | ............. | 128/205.11 |
| 5,460,175 A * | 10/1995 | Foote et al. | .............. | 128/205.24 |
| 5,575,283 A * | 11/1996 | Sjoestrand | ............... | 128/204.23 |
| 5,664,563 A * | 9/1997 | Schroeder et al. | ....... | 128/204.25 |
| 5,674,382 A * | 10/1997 | Chapman | ..................... | 210/96.1 |
| 5,727,545 A * | 3/1998 | Psaros | ...................... | 128/203.12 |

(Continued)

FOREIGN PATENT DOCUMENTS

DE          24 55 751          3/1976

(Continued)

*Primary Examiner* — Justine Yu
*Assistant Examiner* — Latoya M Louis
(74) *Attorney, Agent, or Firm* — McGlew and Tuttle, P.C.

(57) ABSTRACT

A gas-mixing device for respirators can be used both in stationary operation and in mobile operation. The gas-mixing device has a storage tank (5), into which compressed air and oxygen can be introduced by dispensing valves (3, 8). In addition, a blower (10), which draws in gas from the environment (11), is connected to the storage tank (5). To dispense gas from the pressurized gas sources (4, 6) by means of the dispensing valves (3, 8), a first operating pressure level is set in the storage tank (5). When changing over to the blower operation, the operating pressure level is lowered to a pressure level adapted to the maximum respiration pressure.

15 Claims, 1 Drawing Sheet

U.S. PATENT DOCUMENTS

| | | |
|---|---|---|
| 5,848,591 A | 12/1998 | Weismann |
| 5,865,206 A * | 2/1999 | Steigman et al. ............... 137/7 |
| 6,253,780 B1 * | 7/2001 | Salvoni et al. ................. 137/3 |
| 6,412,483 B1 * | 7/2002 | Jones et al. ............ 128/205.11 |
| 6,467,478 B1 * | 10/2002 | Merrick et al. ......... 128/203.25 |
| 2003/0172931 A1 * | 9/2003 | Kerechanin et al. ..... 128/204.18 |
| 2005/0247311 A1 | 11/2005 | Vacchiano et al. |

FOREIGN PATENT DOCUMENTS

DE        197 08 094        1/1998

\* cited by examiner

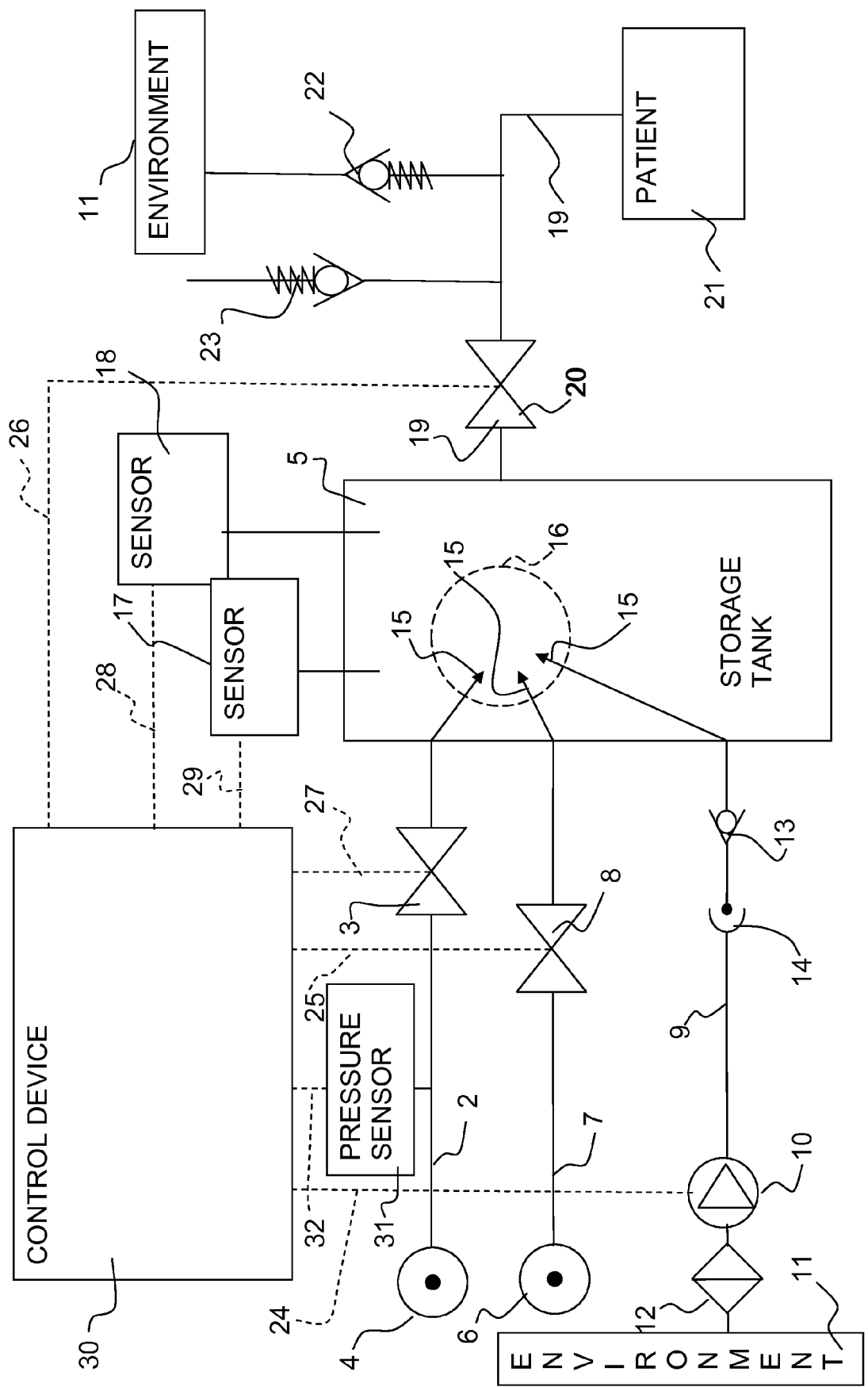

GAS-MIXING DEVICE FOR RESPIRATORS

CROSS REFERENCE TO RELATED APPLICATIONS

This application claims the benefit of priority under 35 U.S.C. §119 of German Patent Application DE 10 2006 055 779.4 filed Nov. 25, 2006, the entire contents of which are incorporated herein by reference.

FIELD OF THE INVENTION

The present invention pertains to a gas-mixing device for respirators and to a process for dispensing medical gases.

BACKGROUND OF THE INVENTION

Respirators are designed for different types of breathing gas sources depending on their field of use. Stationary respirators in hospitals are usually designed for being connected to a central gas supply system. If such a gas supply is not available, pressurized gas cylinders are used. Respirators that are designed mainly for mobile use make use of a blower, which draws in room air and feeds it directly to the patient while oxygen is possibly added.

A gas mixer for a respirator intended to be connected to pressurized gas sources is known from DE 24 55 751 B. Two pressurized gas sources are connected in the prior-art gas mixer to a storage tank via two feed lines and corresponding dispensing valves. The gas mixture is sent from the storage tank to the patient by means of a mixed gas line, which originates from the storage tank and likewise has a dispensing valve. To set a predetermined gas mixture, the dispensing valve is at first opened in one of the feed lines until the outlet pressure in the storage tank has increased to a first predetermined pressure value. The dispensing valve is then closed and the dispensing valve in the second feed line is opened until a second pressure value is reached. A defined volume of gas mixture is then removed via the mixed gas line until the outlet pressure in the storage tank has again become established. The prior-art gas mixture is suitable for use as long as a sufficient pressurized gas supply pressure can be made available.

DE 197 08 094 C2 discloses a respirator, in which ambient air is drawn in with a blower to supply the patient with gas and is compressed until the inspiration pressure necessary for respirating a patient becomes established. Oxygen can be added into a storage tank, which receives the ambient air drawn in, so that different oxygen concentrations can be set in the breathing gas. No provisions are made for operation with pressurized gases alone from a pressurized gas supply system in the case of this respirator.

SUMMARY OF THE INVENTION

The basic object of the present invention is to improve a device of the type mentioned such that both stationary and mobile operation are possible and to provide a process for dispensing medical gases.

According to the invention, a device for mixing gases for respirators is provided with a first feed line and a first dispensing valve for a first gas, with a second feed line and a second dispensing valve for a second gas, with a third feed line with a blower for drawing in ambient air and with a storage tank, to which the feed lines are connected. A directional valve in the third feed line on the incoming flow side of the storage tank makes possible a gas flow from the blower into the storage tank and interrupts a gas flow from the storage tank into the third feed line. A mixed gas line extends from the storage tank with a mixed gas dispensing valve. A pressure sensing means is provided for sensing the pressure in the storage tank. A control device is in functional connection with the dispensing valves, the blower and the pressure sensing means. The control device is designed to set a first operating pressure level in the storage tank in a first mode of operation with dispensing of gas via the dispensing valves, and to lower the first operating pressure level to a second operating pressure level in a second mode of operation with dispensing of gas via the third feed line.

The advantage of the present invention is essentially that in case of stationary operation, pressurized gases are taken from a stationary pressurized gas supply unit and dispensed into a storage tank at a predetermined operating pressure level. Broad dynamic changes can be achieved with this mode of operation, because the gas volume needed for beginning the inspiration without delay can be taken directly from the storage tank. The gas volume from the storage tank is available without a time delay, so that a constantly high quality of respiration is achieved.

For mobile use, the operating pressure level in the storage tank is lowered to a lower value, and the breathing gas is drawn in from the environment by means of a blower. In addition, oxygen may be added to the ambient air via one of the feed lines. It is also possible as a result to obtain gas mixtures with oxygen concentrations above 21%. The operating pressure level in the storage tank is set in case of blower operation such that the maximum respiration pressure can be applied. It is possible by means of the blower to take a sufficiently large gas volume from the environment to generate an inspiration stroke.

The process according to the present invention is characterized by the following steps:

a first gas and a second gas are introduced into a storage tank from pressurized gas sources with dispensing valves;

a gas mixture is taken from the storage tank via a mixed gas line and a mixed gas dispensing valve;

the dispensing valves are operated with a control device such that a predetermined first operating pressure level becomes established in the storage tank;

a blower, which draws in ambient air, is connected to the storage tank; and the first operating pressure level is lowered to a predetermined second operating pressure level when the blower feeds ambient air into the storage tank.

The storage tank of the gas-mixing device according to the present invention is designed such that its inner volume is between 200 mL and 2,000 mL. The operating pressure level in the storage tank is set such by means of the control device that the first operating pressure level is in the range around 400 mbar and the second operating pressure level has a value of about 50 mbar. The second operating pressure level is derived from the maximum respiration pressure needed. The second operating pressure level is preferably in a range between 40 mbar and 100 mbar.

The pressure in the storage tank is measured directly with a pressure sensor in the simplest case. As an alternative, it is possible to derive the pressure indirectly from the current intensity that is needed to open a mixed gas dispensing valve arranged downstream of the storage tank. The opening current depends on the pressure in the storage tank.

Oxygen and compressed air are fed as pressurized gases into the storage tank. However, additionally introducing laughing gas as a pressurized gas into the storage tank for other applications, for example, in the area of anesthesia, is also within the scope of the present invention.

Provisions are made according to the present invention for arranging a monitoring device for detecting the compressed air supply pressure in the area of a first dispensing valve, which dispenses compressed air into the storage tank. When the compressed air supply pressure drops below a predetermined threshold value, the pressure level in the storage tank is lowered by the control device to the second operating pressure level and operation is changed over to blower operation. As a result, respiration of the patient is guaranteed by drawing in breathing gas from the environment even in case of a drop of the compressed air supply pressure. In the simplest case, the monitoring device is a pressure-measuring device, which detects the supply pressure on the incoming flow side of the first dispensing valve. As an alternative, the gas flow through the first dispensing valve can be measured at a certain degree of opening of the first dispensing valve. If it is determined now that the gas flow is below a predetermined threshold value relative to a certain cross-sectional area of the dispensing valve, which cross-sectional area is decisive for the gas flow, this is an indicator of the drop in the compressed air supply pressure.

Provisions are made according to the present invention for the feed lines to be arranged within the storage tank such that their gas discharge openings are directed towards each other, i.e., they open into a so-called mixing area. Intensive mixing of the gas components shall be achieved due to the individual gas flows meeting each other in the mixing area to obtain a homogeneous gas mixture in the mixed gas line.

An exemplary embodiment of the present invention is shown in the FIGURE and will be explained in more detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWING

In the drawing:
The only FIGURE is a schematic view of a gas-mixing device for respirators according to the invention.

DESCRIPTION OF THE PREFERRED EMBODIMENT

Referring to the drawing in particular, the only FIGURE schematically shows a gas-mixing device 1 for at least two gases. A first feed line 2 with a first dispensing valve 3 is connected to a first pressurized gas source 4 for compressed air and opens into a storage tank 5. Oxygen is introduced into the storage tank 5 from a second pressurized gas source 6 for oxygen with a second feed line 7 and a second dispensing valve 8. A third feed line 9 extends from a blower 10, which draws air from the environment 11 via a filter 12 to the storage tank 5 via a plug coupling 14 and a nonreturn valve 13. The nonreturn valve 13 prevents mixed gas from flowing back from the storage tank 5. The feed lines 2, 7, 9 are directed in a star-shaped pattern within the storage tank 5 such that their discharge openings 15 open into a mixing area 16 in order to guarantee a direct mixing of the gas components in a predetermined volume of the storage tank 5.

A first pressure sensor 17 measures the pressure within the storage tank 5 and an oxygen sensor 18 detects the oxygen concentration in the mixed gas. The gas mixture is fed to a patient 21 via a mixed gas line 19 and a mixed gas dispensing valve 20. The mixed gas dispensing valve 20 is of a pressure-compensated design, so that no resulting forces act on the valve lifter, which is not shown in more detail. In addition, admission pressure compensation is provided in such a way that the mixed gas dispensing valve 20 closes in case of power failure.

A safety switching group with nonreturn valves 22, 23 arranged at the mixed gas line 19 such that they act in opposite directions limits the pressure in the mixed gas line 19 to a maximum pressure and makes it possible, on the other hand, in case of failure of the gas supply, to take gas directly from the environment 11. The dispensing valves 3, 8, 20, the blower 10 and the sensors 17, 18 are connected to a control device 30 via data lines 24, 25, 26, 27, 28, 29. The compressed air supply pressure in the first feed line 2 is determined with a second pressure sensor 31 and transmitted to the control device 30 via the data line 32.

The gas-mixing device according to the present invention operates as follows:

In case of operation from a central gas supply system, oxygen and compressed air are fed into the storage tank 5 via the dispensing valves 3, 8. Flow-controlled valves, with which a predetermined operating pressure level is set in the storage tank 5, are used as dispensing valves 3, 8. The operating pressure level is monitored with the first pressure sensor 17.

Corresponding to the gas volumes of air and oxygen fed in, a certain oxygen concentration becomes established in the storage tank 5, which is measured with the oxygen sensor 18. In case of operation from the pressurized gas sources 4, 6, the operation is usually carried out with an operating pressure level of 400 mbar in the storage tank 5. The volume of the storage tank 5 is on the order of magnitude of about 700 mL. Thus, a sufficiently large gas volume is available for beginning the inspiration stroke without delay.

In case of mobile operation of the gas-mixing device 1, the operating pressure level in the storage tank 5 is lowered to 50 mbar and air is drawn in from the environment 11 with the blower 10. The first dispensing valve 3 is closed now. If oxygen is to be added in mobile operation, a corresponding pressurized oxygen source 6 may be carried along, from which oxygen can be introduced into the storage tank 5 with the second dispensing valve.

The changeover to the second operating pressure level is also carried out in case of operation from a central compressed air supply system when a drop in the compressed air supply is detected. The second pressure sensor 31 is arranged for this purpose in the first feed line in order to monitor the supply pressure. If the second pressure sensor 31 detects a drop in the supply pressure to below a predetermined threshold value, the operating pressure level in the storage tank 5 is lowered to a value of about 50 mbar and the blower 10 is turned on for supplying the patient with breathing gas. The second operating pressure level arises from the maximum respiration pressure that is needed during the inspiration stroke.

While a specific embodiment of the invention has been shown and described in detail to illustrate the application of the principles of the invention, it will be understood that the invention may be embodied otherwise without departing from such principles.

What is claimed is:

1. A device for mixing gases for respirators, the device comprising:
    a gas storage tank;
    a first gas source;
    a first feed line and a first dispensing valve for said first gas source, said first feed line being connected to said gas storage tank and providing a gas flow passage from said first gas source to said gas storage tank via said first dispensing valve;
    a second gas source;
    a second feed line and a second dispensing valve for said second gas source, said second feed line being connected to said gas storage tank and providing a gas flow passage from said second gas source to said gas storage tank via said second dispensing valve;
    a third feed line with a blower for drawing in ambient air, said third feed line being connected to said gas storage tank;
    a directional valve in said third feed line on an incoming flow side of said gas storage tank, said directional valve making possible a gas flow from said blower into said gas storage tank and interrupting a gas flow from said gas storage tank into said third feed line;
    a mixed gas line extending from said gas storage tank, said mixed gas line having a mixed gas dispensing valve;
    a pressure sensing means for sensing gas pressure in said gas storage tank;
    a control device in functional connection with each of said first dispensing valve and said second dispensing valve, with said blower and with said pressure sensing means, the control device setting a first operating pressure level in said gas storage tank in a first mode of operation with dispensing of gas into said gas storage tank via said first dispensing valve and said second dispensing valve, and operating said blower and lowering the first operating pressure level to a second operating pressure level in a second mode of operation with dispensing of gas into said gas storage tank via said third feed line.

2. A device in accordance with claim 1, wherein said gas storage tank has a volume between 200 mL and 2,000 mL.

3. A device in accordance with claim 1, wherein the first operating pressure level is in a range around 400 mbar and the second operating pressure level is in a range between 40 mbar and 100 mbar.

4. A device in accordance with claim 1, wherein said first feed line is connected to a pressurized gas source as said first gas source.

5. A device in accordance with claim 1, wherein said second feed line is connected to an oxygen source as said second gas source.

6. A device in accordance with claim 4, further comprising a monitoring device, in functional connection with said control device, for detecting compressed air supply pressure present in said first feed line in an area of said first dispensing valve, said control device changing over to the second operating pressure level with blower operation when the pressure detected by said monitoring device drops below a predetermined threshold value.

7. A device in accordance with claim 1, wherein:
    said gas storage tank has a mixing area;
    said first feed line has a gas discharge opening;
    said second feed line has a gas discharge opening;
    said third feed line has a gas discharge opening; and
    each gas discharge opening extends within said gas storage tank to said mixing area.

8. A device in accordance with claim 1, wherein said first feed line is connected to a pressurized gas source as said first gas source and said second feed line is connected to an oxygen source as said second gas source and further comprising:
    a monitoring device, in functional connection with said control device, for detecting the compressed air supply pressure present in said first feed line upstream of said first dispensing valve, said control device changing over to the second operating pressure level with blower operation when the pressure detected by said monitoring device drops below a predetermined threshold value.

9. A process for mixing gases for respirators, the process comprising the steps of:
    providing a gas storage tank;
    providing a first gas source;
    providing a first feed line and a first dispensing valve for said first gas source, said first feed line being connected to said gas storage tank and providing a gas flow passage from said first gas source to said gas storage tank via said first dispensing valve;
    providing a second gas source;
    providing a second feed line and a second dispensing valve for said second gas source, said second feed line being connected to said gas storage tank and providing a gas flow passage from said second gas source to said gas storage tank via said second dispensing valve;
    providing a third feed line with a blower for drawing in ambient air, said third feed line being connected to said gas storage tank;
    providing a directional valve in said third feed line between said blower and said gas storage tank on an incoming flow side of said gas storage tank, said directional valve making possible a gas flow from said blower into said gas storage tank and interrupting a gas flow from said gas storage tank into said third feed line;
    providing a mixed gas line extending from said gas storage tank, said mixed gas line having a mixed gas dispensing valve;
    sensing gas pressure in said gas storage tank;
    actuating the pressurized gas source dispensing valves with a control device such that a first operating gas pressure level becomes established in the gas storage tank in a first mode of operation;
    in a second mode of operation, operating the blower to feed ambient air into said gas storage tank; and
    lowering the first operating pressure level to a second operating pressure level when the blower feeds ambient air into said gas storage tank.

10. A process in accordance with claim 9, wherein said gas storage tank has a volume between 200 mL and 2,000 mL.

11. A process in accordance with claim 9, wherein the first operating pressure level is in a range around 400 mbar and the second operating pressure level is in a range between 40 mbar and 100 mbar.

12. A process in accordance with claim 9, wherein said first feed line is connected to a pressurized gas source as said first gas source.

13. A process in accordance with claim 12, further comprising:
    providing a monitoring device, in functional connection with said control device, for detecting compressed air supply pressure present in said first feed line; and detecting compressed air supply pressure present in an area of said first dispensing valve with said monitoring device, said control device changing over to the second operating pressure level with blower operation when the pressure detected by said control device drops below a predetermined threshold value.

14. A process in accordance with claim 9, wherein said second feed line is connected to an oxygen source as said second gas source.

15. A process in accordance with claim 9, wherein:
said gas storage tank has a mixing area;
said first feed line has a gas discharge opening;
said second feed line has a gas discharge opening;
said third feed line has a gas discharge opening; and
each gas discharge opening extends within said gas storage tank to said mixing area.

* * * * *